United States Patent [19]

Cantatore

[11] Patent Number: 4,695,599
[45] Date of Patent: Sep. 22, 1987

[54] USE OF DIPIPERIDINE-DI-CARBAMATES AS STABILIZERS FOR SYNTHETIC POLYMERS

[75] Inventor: Giuseppe Cantatore, Bitonto, Italy

[73] Assignee: Ciba-Geigy Corporation, Ardsley, N.Y.

[21] Appl. No.: 783,804

[22] Filed: Oct. 4, 1985

Related U.S. Application Data

[63] Continuation of Ser. No. 606,456, May 2, 1984, abandoned.

[30] Foreign Application Priority Data

May 3, 1983 [IT] Italy ............................. 20900 A/83

[51] Int. Cl.$^4$ .............................................. C08K 5/34
[52] U.S. Cl. .................................. 524/103; 546/187; 546/188; 546/189
[58] Field of Search .................. 546/187, 188, 189; 524/103

[56] References Cited

U.S. PATENT DOCUMENTS

| 3,904,581 | 9/1975 | Murayama et al. | 524/103 |
| 4,210,576 | 7/1980 | Di Battista et al. | 524/103 |
| 4,369,321 | 1/1983 | Cantatore | 546/188 |
| 4,395,508 | 7/1983 | Nelli et al. | 524/103 |

Primary Examiner—John Kight
Assistant Examiner—Kriellion Morgan
Attorney, Agent, or Firm—Wenderoth, Lind & Ponack

[57] ABSTRACT

The use of piperidine compounds of the formula

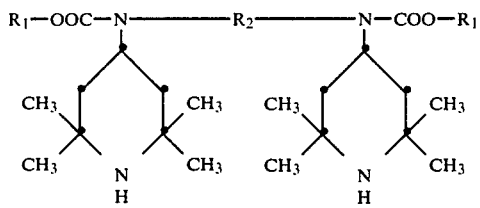

as light stabilizers, heat stabilizers and oxidation stabilizers is described.

8 Claims, No Drawings

USE OF DIPIPERIDINE-DI-CARBAMATES AS STABILIZERS FOR SYNTHETIC POLYMERS

This application is a continuation of now abandoned application Ser. No. 606,456, filed May 2, 1984.

The present invention relates to the use of the dipiperidine compounds of the formula

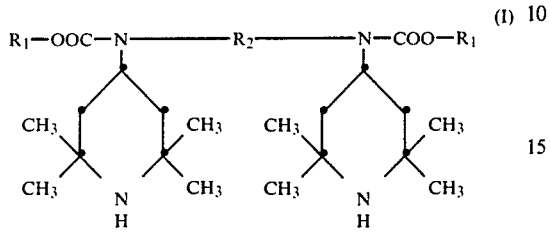

in which $R_1$ is $C_1$-$C_{12}$-alkkenyl, $C_3$-$C_{12}$-alkenyl, $C_5$-$C_{12}$-cycloalkyl, or phenyl or hydroxphenyl which are unsubstituted or substituted by 1 to 3 $C_1$-$C_4$-alkyl groups or by benzyl or hydroxybenzyl which are unsubstituted or substituted by 1 to 3 $C_1$-$C_4$- alkyl groups, $R_2$ is $C_1$-$C_{18}$ -alkylene, $C_5$-$C_{18}$ -cycloalkylene, $C_6$-$C_{18}$ -arylene, $C_7$-$C_{18}$-aralkylene or a radical of the formula (II)

 (II)

in which $R_3$ and $R_4$, which can be identical or diferrent, are $C_2$-$C_6$-alkylene, n is 1 or 2 and X is —O—or

with $R_5$ being $C_1$-$C_{12}$-alkyl, $C_5$-$C_{12}$- cycloalkyl, $C_6$-$C_{12}$-aryl, $C_6$-$C_{12}$-aralkyl, 2,2,6,6,-tetramethylpiperidin-4-yl or a radical —COOR$_1$ in which $R_1$ is as defined above, as light stabilisers, heat stabilisers and oxidation stabilisers for synthetic polymers.

Illustrative examples of the meanings of the various radicals in the formula (I) are as follows:

for $R_1$: methyl, ethyl, propyl, isopropyl, butyl, tert.-butyl, sec.-butyl, hexyl, 2-ethylhexyl, octyl, 1,1,3,3-tetramethylbutyl, decyl, dodecyl, allyl, methallyl, but-2-enyl, undec-l0-enyl, cyclohexyl, 2- or 4-methylcyclohexyl, 3,3,5-trimethylcyclohexyl, cyclooctyl, cyclododecyl, phenyl, o-, m- and p-methylphenyl, 2,6-dimethylphenyl, 2,4,6-trimethylphenyl, 4-t-butylphenyl, 4-t-octylphenyl, 4-methoxyphenyl, 4-ethoxyphenyl, 3,5-di-t-butyl-4-hydroxyphenyl, benzyl, 4-methylbenzyl, 4-hydroxybenzyl and 3,5-di-t-butyl-4-hydroxybenzyl;

for $R_2$: methylene, ethylene, 1,2- and 1,3-propylene, 2-hydroxy-1,3-propylene, tetramethylene, pentamethylene, 2,2-dimethyl-1,3-propylene, hexamethylene, decamethylene, dodecamethylene, cyclohexylene, cyclohexylenedimethylene, phenylene and xylylene;

for $R_3$ and $R_4$: ethylene, 1,2- or 1,3-propylene, tetramethylene and hexamethylene; and for $R_5$ methyl, ethyl, propyl, isopropyl, butyl, tert.-butyl, sec.-butyl, hexyl, 2-ethylhexyl, octyl, 1,1,3,3-tetramethylbutyl, decyl, dodecyl, cyclohexyl, 2- or 4-methylcyclohexyl, 3,3,5trimethylcyclohexyl, cyclooctyl, cyclododecyl, phenyl, o-, m-and p-methylphenyl, 2,6-dimethylphenyl, 2,4,6-trimethylphenyl, 4-t-butylphenyl, 4-(1,1,3,3-tetramethylbutyl)-phenyl, 4-methoxyphenyl, 4-ethoxyphenyl, 3,5-di-t-butyl-4-hydroxyphenyl, benzyl, 4-methylbenzyl, 4-hydroxybenzyl, 3,5-d-t-butyl-4-hydroxybenzyl and 2,2,6,6-tetramethyl-piperidin-4-yl.

Those compounds of the formula (I) are preferred in which $R_1$ is $C_1$-$C_8$-alkyl, $C_3$-$C_8$-alkenyl, cyclohexyl, phenyl or benzyl, $R_2$ is $C_1$-$C_6$-alkylene, cyclohexylene, phenylene or xylylene, $R_3$ and $R_4$ are $C_2$-$C_4$-alkylene and $R_5$ is a radical —COOR$_1$ in which $R_1$ is as defined above.

Particularly preferred compounds of the formula (I) are those in which $R_1$ is $C_1$-$C_4$-alkyl and $R_2$ is $C_2$-$C_6$-alkylene.

The compounds of formula I, wherein $R_1$ is neither methyl or ethyl, i.e. where $R_1$ is $C_3$-$C_{12}$-alkyl, $C_3$-$C_{12}$-alkenyl, $C_5$-$C_{12}$-cycloalkyl or phenyl or hydroxyphenyl which are unsubstituted or substituted by 1 to 3 $C_1$-$C_4$-alkyl groups or by benzyl or hydroxybenzyl which are unsubstituted or substituted by 1 to 3 $C_1$-$C_4$-alkyl groups, are new and thus constitute a further embodiment of the present invention.

The compounds of the formula (I) can be prepared by known processes, by reacting a compound of the formula (III)

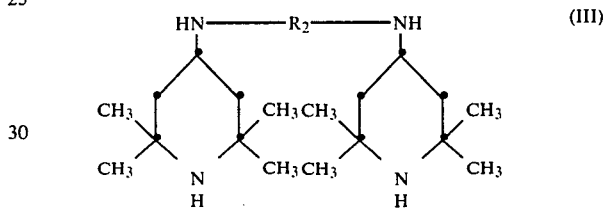 (III)

in which $R_2$ is as defined above, with a chlorocarbonate of the formula (IV)

 (IV)

in which $R_1$ is as defined above, in an organic solvent and in the presence of an organic or inorganic base, such as pyridine, triethylamine, tributylamine, sodium hydroxide, potassium hydroxide, sodium carbonate or potassium carbonate, at a temperature between —30° and 30° C., preferably between —20° and 20° C.

In order to illustrate the present invention more clearly, some examples of the preparation of compounds of the formula (I) are described; these examples are given by way of illustration and do not imply any restriction of the invention.

EXAMPLE 1

Preparation of N,N'-bis-(ethoxycarbonyl)-N,N'-bis-(2,2,6,6-tetramethyl-piperidrn-4-yl)-hexamethylenediamine.

22,8 g (0.21 mol) of ethyl chlorocarbonate are added, at a temperature not exceeding 0° C. to a solution, cooled to —10° C., of 39.4 g (0.1 mol) of N,N'-bis-(2,2,6,6-tetramethylpiperidin-4-yl)hexamethylenediamine in 200 ml of 1,2-dichloroethane. 8.4 g of sodium hydroxide dissolved in 50 ml of water are then added slowly, the temperature being maintained at 0° C. The temperature is then allowed to rise to 20° C., the aqueous phase is separated off, and the organic phase is washed with water. After drying over anhydrous Na$_2$SO$_4$ and removal of the solvent, the residue is crystallised from octane.

The product obtained melts at 125° C.

Analysis for $C_{30}H_{58}N_4O_4$:

| calculated %: | C 66.87; | H 10.85; | N 10.40 |
|---|---|---|---|
| found %: | C 66.02; | H 10.73; | N 10.35 |

EXAMPLES 2–12

The procedure of Example 1 is repeated for preparing the following compounds of the formula (I):

| Example No. | $R_1$ | $R_2$ | Melting point (°C.) |
|---|---|---|---|
| 2 | methyl | —(CH$_2$)$_2$— | 200 |
| 3 | ethyl | —(CH$_2$)$_2$— | 161 |
| 4 | isopropyl | —(CH$_2$)$_2$— | 156 |
| 5 | n-butyl | —(CH$_2$)$_2$— | 124 |
| 6 | allyl | —(CH$_2$)$_2$— | 141 |
| 7 | methyl | —(CH$_2$)$_3$— | 130 |
| 8 | ethyl | —(CH$_2$)$_3$— | 84 |
| 9 | methyl | —(CH$_2$)$_6$— | 125 |
| 10 | isopropyl | —(CH$_2$)$_6$— | 116 |
| 11 | ethyl | —(CH$_2$)$_2$—N—(CH$_2$)$_2$—<br>                  |<br>                COOC$_2$H$_5$ | 103 |
| 12 | allyl | —(CH$_2$)$_6$— | 91 |

As mentioned at the outset, the compounds of the formula (I) are very effective in improving the light stability, heat stability and oxidation stability of synthetic polymers, for example high-density and low-density polyethylene, polypropylene, ethylene/propylene copolymers, ethylene/vinyl acetate copolymers, polybutadiene, polyisoprene, polystyrene, butadiene/styrene copolymers, vinyl chloride/vinylidene chloride polymers and copolymers, polyoxymethylene, polyurethanes, saturated and unsaturated polyesters, polyamides, polycarbonates, polyacrylates, alkyd resins and epoxide resins as well as lacquers.

The compounds of the formula (I) can be mixed with the synthetic polymers in various proportions depending on the nature of the polymer, the end use and the presence of other additives. In general, it is advantageous to employ from 0.01 to 5% by weight of the compounds of the formula (I), relative to the weight of the polymers, preferably from 0.05 to 1%.

The compounds of the formula (I) can be incorporated into the polymeric materials by various processes, such as dry blending in the form of powders, or wet mixing in the form of solutions or suspensions, or mixing in the form of a master batch; in these operations, the synthetic polymer can be employed in the form of a powder, granules, a solution, a suspension or in the form of a latex. The polymers stabilised with the products of the formula (I) can be used for the preparation of moulded articles, films, tapes, fibres, monofilaments, surface coatings and the like.

If desired, other additives, such as antioxidants, ultraviolet absorbers, nickel stabilisers, pigments, fillers, plasticisers, antistatic agents, flameproofing agents, lubricants, anti-corrosion agents and metal deactivators, can be added to the mixtures of the compounds of the formula (I) with the synthetic polymers.

Examples of additives which can be mixed with the compounds of the formula (I) are, in particular:
1. Antioxidants
1.1. Alkylated monophenols, for example, 2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4methylphenol
2-(α-methylcyclohexyl)-4,6-dimethylphenol
2,6-di-octadecyl-4-ethylphenol
2,4,6-tri-cyclohexylphenol
2,6-di-tert.butyl-4methoxymethylphenol
  1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol
  1.3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)
  1.4. Alkyliden-bisphenols, for example,
2,2'-methylene-bis-(6-tert.butyl-4-methylphenol)
2,2'sethylene-bis-(6-tert.butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzly)-4-nonylphenol]
2,2'-methylene-bis- (4, 6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl)-butane
2,6-di-(3-tert.butyl-5-methyl-2-hydroxybenzyl)-4-methylphenol
1,1,3-tris-(5-tert.butyl-4-hydroxy-2sethylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)-butyrat]
di-(3-tert.butyl-4-hydroxy-5-methylphenyl)-dicyclopentadien
di-[2-(3'-tert.butyl-2'-hydroxy-5'methyl-benzyl)-6-tert.butyl-4-methlphenyl]-terephtha
  1.5. Benzylcompounds, for example,
1,3,5-tri-(3,5-di-tert.butyl-4-hydroxybenzyl)-2,4,6-trimethyl-benzene-di-(3,5-di-tert.butyl-4-hydroxybenzyl)-sulfide
3,5-di-tert.butyl-4-hydroxybenzyl-mercapto-acetic acid-isooctyl ester
bis-(4-tert.butyl-3-hydroxy-2,6-dimethylbenzyl)dithiol-terephthalate
1,3,5-tris-(3,5-di-tert.butyl-4-hydroxybenzyl)-isocyanurate
1,3,5-tris-(4-tert.butyl-3-hydroxy-2,6-dimethylbenzyl)-isocyanurate
3,5-di-tert.butyl-4-hydroxybenzyl-phosphoric acid-dioctadecyl ester
3,5-di-tert.butyl-4-hydroxybenzyl-phosphoric acid-monoethyl ester, calcium-salt
  1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-triazine octyl-N-(3,5-di-tert.butyl-4-hydroxyphenyl)-carbaminate 1.7. Esters of β-(3,5-di-tert.butyl-4-hydroxyphenyl)-propionic acid with monohydric or polyhydric alcohols, for example,

| | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.8. Ester of β- (5-tert.butyl-4-hydroxy-3-methylphenyl)propionic acid with monohydric or polyhydric alcohols, for example,

| | |
|---|---|
| methanol | diethyleneglycol |
| octadecanol | triethyleneglycol |
| 1,6-hexanediol | pentaerytritol |
| neopentylglycol | tris-hydroxyethyl isocyanorate |
| thiodiethyleneglycol | di-hydroxyethyl oxalic acid diamide |

1.9. Amides of β-3,5-di-tert.butyl-4-hydroxyphenyl)-propionic acid for example,
N,N'-di-(3,5-di-tert.butyl-4-hydroxyphenylpropionyl)-hexamethylendiamine
N,N'-di-(3,5-di-tert.butyl-4-hydroxyphenylpropionyl)-trimethylendiamine
N,N'-di-(3,5-di-tert.butyl-4-hydroxyphenylpropionyl)-hydrazine 2. UV absorbers and light stabilisers 2.1. 2-(2'-Hydroxyphenyl)-benztriazoles, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl, 3'-sec.butyl-5'-tert.butyl-, 4'-octoxy-, 3', 5'-di-tert.amyl-, 3',5'-bis-(α,α-dimethylbenzyl)-derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxyderivative.

2.3. Esters of optionally substituted benzoic acids for example, phenyl salicylate, 4-tert.butyl-phenylsalicilate, octylphenyl salicylate, dibenzoylresorcinol, bis-(4-tert.butylbenzoyl)-resorcinol, benzoylresorcinol3,5-di-tert.-butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β, β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1-,1,3,3-tetramethylbutyl)-phenol], such as the 1:1 or 1:2 complex optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate bis-(1,2,2,6,6-pentamethylpiperidyl)-sebacate n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)hexamethylendiamine and 4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone).

2.7. Oxalic acid diamides, for example, 4,4'-dioctyloxy-oxanilide, 2,2'-di-octyloxy-5,5'-di-tert.butyloxanilide, 2,2'-di-dodecyloxy-5,5'-di-tert.butyl-oxanilide, 2-ethoxy-2'-ethyl-oxanilide, N,N'-bis-(3-dimethylaminopropyl)-oxalamide, 2-ethoxy-5-tert.butyl-2'-ethyloxanilide and its mixture with 2-ethoxy-2'-ethyl-5,4'-di-tert.butyloxanilide and mixtures of ortho-and para-methoxy- as well as of o- and p-ethoxy-disubstituted oxanilides.

3. Metal deactivators, for example, N,'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)hydrazine, 3-salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythrit diphosphite, tris-(2,4-di-tert.butylphenyl) phosphite, di-isodecylpentaerythrit diphosphite, di-(2,4-di-tert.butylphenyl)pentaerythrit diphosphite, tristearylsorbite triphosphite, tetrakis-(2,4-di-tert.butylphenyl)-4,4'-biphenylylen diphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythrit-tetrakis-(β-dodecylmercapto)-propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

The efficiency, as stabilisers, of the products prepared according to the present invention is illustrated in the examples which follow, in which some of the products obtained in the preparation examples are employed for stabilising tapes and sheet.

Some of the compounds of the formula (1) were already known as intermediates for the preparation of a class of stabilisers for polymers, which are the subject of U.S. Pat. No. 4,369,321 by the same Applicant. Surprisingly, it was found that these compounds themselves can be used as stabilisers for synthetic polymers and are even more effective in some applications than the stabilisers of the abovementioned patent application.

The majority of the compounds of the formula (I) are novel.

EXAMPLE 13

In each case, 0.5 g of the products indicated in Table 1, 1 g of pentaerythritol tetrakis-3-(3,5-di-t-butyl-4-hydroxyphenyl)-propionate, 1 g of calcium stearate, 1 g of a pigment masterbatch Blue ((R)Filofin Blue 600 of CIBA-GEIGY) and 1,000 g of polypropylene powder of melt index 3 ((R)Propathene HF 18, a product of Imperial Chemical Industries) are intimately mixed in a slow mixer. The mixtures obtained are extruded at a temperature of 200°-220° C. to give granules of polymer, which are then converted into 2 mm thick sheet by compression-injection at 250° C.

The sheet obtained is exposed in a Weather-Ometer model 65 WR (ASTM G 27-70), with a black panel temperature of 63° C., up to the onset of surface frosting (chalking).

For comparison, a polypropylene sheet prepared under the same conditions as indicated above, but without the addition of the compounds according to the invention, is exposed. The exposure time (in hours) required for such an onset of frosting is indicated in Table 1.

TABLE 1

| Stabiliser | Frosting time (hours) |
|---|---|
| none | 500 |
| compound of Example 1 | 1,810 |
| compound of Example 4 | 1,600 |

EXAMPLE 14

1 g of each of the compounds indicated in Table 2, 1 g of pentaerythritol tetrakis-3-(3,5-di-t-butyl-4-hydroxyphenyl)-propionate, 1 g of calcium stearate, 1 g of a pigment masterbatch (Filofin Blue 600 of CIBA-GEIGY) and 1,000 g of polypropylene powder of melt index 3 (Propathene HF 18, a product of the Imperial Chemical Industries) are intimately mixed in a slow mixer.

The mixture obtained is then extruded at a temperature of 200°-220° C., to give granules of polymer, which are then converted into 2 mm thick plaques by compression-injection at 250° C.

The plaques obtained are exposed, on a white card, in a Weather-Ometer 65 WR (ASTM G27-70) whith a black panel temperature of 63° C., up to the onset of surface frosting (chalking).

For comparison, polypropylene plaques prepared under the same conditions as indicated above, but without the addition of the compounds according to the invention, are exposed.

The exposure time (in hours) required for such an onset of frosting is indicated in Table 2.

TABLE 2

| Stabiliser | Frosting time (in hours) |
|---|---|
| none | 500 |
| compound of Example 1 | 2,850 |
| compound of Example 2 | 2,690 |
| compound of Example 3 | 2,850 |
| compound of Example 5 | 2,505 |
| compound of Example 7 | 2,940 |
| compound of Example 8 | 2,690 |
| compound of Example 9 | 2,850 |
| compound of Example 10 | 2,690 |
| compound of Example 11 | 2,510 |

What is claimed is:

1. A light-stabilised, heat-stabilised and oxidation-stabilised polymer composition, which comprises a synthetic polymer and a stabilizing amount of one or more of the stabilisers of the formula (I)

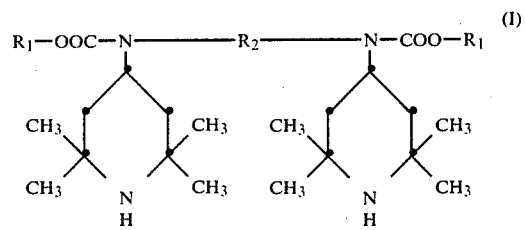

in which $R_1$ is $C_1-C_{12}$-alkyl, $C_3-C_{12}$-alkenyl, $C_5-C_{12}$-cycloalkyl or phenyl or hydroxyphenyl which are unsubstituted or substituted by 1 to 3 $C_1-C_4$-alkyl groups or by benzyl or hydroxybenzyl which are unsubstituted or substituted by 1 to 3 $Cl_1-C_4$-alkyl groups, $R_2$ is $C_1-C_{18}$-alkylene, $C_5-C_{18}$-cycloalkylene, $C_6-C_{18}$-arylene, $C_7-C_{18}$-aralkylene or a radical of the formula (II)

$$-R_3 + X - R_4 +_n \quad (II)$$

in which $R_3$ and $R_4$, which can be identical or different, are $C_2-C_6$-alkylene, n is 1 or 2 and X is —O— or

with $R_5$ being $C_1-C_{12}$-alkyl, $C_5C_{12}$-cycloalkyl, $C_6-C_{12}$-aryl, $C_7-C_{12}$-aralkyl, 2,2,6,6-tetramethyl-piperidin-4-yl or a radical —$COOR_1$ in which $R_1$ is as defined above.

2. A composition according to claim 1, which comprises a synthetic polymer and one or more of the stabilisers of the formula (I), wherein $R_1$ is $C_1-C_8$-alkyl, $C_3-C_8$-alkenyl, cyclohexyl, phenyl or benzyl, $R_2$ is $C_1-C_6$-alkylene, cyclohexylene, phenylene or xylylene, $R_3$ and $R_4$ are $C_2-C_4$-alkylene and $R_5$ is a radical —$COOR_1$ in which $R_1$ is as defined above.

3. A composition according to claim 1 which comprises a synthetic polymer and one or more of the stabilisers of the formula (I), wherein $R_1$ is $C_1-C_4$-alkyl and $R_2$ is $C_2-C_6$-alkylene.

4. A compostion according to claim 1, wherein the stabiliser is N,N'-bis-(methlxycarbonyl)-N,N'-bis-(2,2,6,6,-tetramethyl-piperidin-4-yl)-hexamethylenediamine.

5. A composition according to claim 1, wherein the stabiliser is N,N'-bis-(ethoxycarbonyl)-N,N'-bis-(2,2,6,6-tetramethyl-piperidin-4yl)-hexamethylenediamine.

6. A composition according to claim 1, which comprises a synthetic polymer and one or more of the stabilisers of the formula (I) in an amount of from 0.01 to 5% by weight, relative to the weight of the synthetic polymer.

7. Composition according to claim 1, which in addition to the stabiliser of the formula (I), comprises other conventional additives for synthetic polymers.

8. A composition according to claim 1, wherein the synthetic polymer is polyethylene or polypropylene.

* * * * *